United States Patent
Ebner et al.

(10) Patent No.: US 8,061,183 B2
(45) Date of Patent: Nov. 22, 2011

(54) PROTECTIVE CAP FOR A GAS SENSOR, AND A GAS SENSOR

(75) Inventors: Joachim Ebner, Munich (DE); Oliver Hausner, Grasbrunn (DE); Bodo Durst, Munich (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 106 days.

(21) Appl. No.: 12/578,069

(22) Filed: Oct. 13, 2009

(65) Prior Publication Data

US 2010/0024524 A1   Feb. 4, 2010

Related U.S. Application Data

(63) Continuation of application No. PCT/EP2008/001991, filed on Mar. 13, 2008.

(30) Foreign Application Priority Data

Apr. 10, 2007   (DE) .......................... 10 2007 016 976

(51) Int. Cl.
  *G01N 7/00* (2006.01)
(52) U.S. Cl. ...................................... 73/23.31; 73/31.05
(58) Field of Classification Search .................. 204/424, 204/425, 426, 427, 428, 429; 73/23.31, 23.32, 73/31.05, 431
See application file for complete search history.

(56) References Cited

U.S. PATENT DOCUMENTS

| | | | |
|---|---|---|---|
| 4,199,424 A | | 4/1980 | Teitelbaum |
| 5,880,353 A | * | 3/1999 | Graser et al. .................. 73/23.2 |
| 7,413,641 B2 | | 8/2008 | Yamada et al. |
| 2005/0016849 A1 | * | 1/2005 | Ikoma et al. .................. 204/429 |
| 2005/0241937 A1 | * | 11/2005 | Shichida et al. .............. 204/424 |
| 2007/0261473 A1 | | 11/2007 | Weyl et al. |
| 2008/0016948 A1 | * | 1/2008 | Yamada ....................... 73/31.05 |
| 2008/0223110 A1 | | 9/2008 | Weyl et al. |

FOREIGN PATENT DOCUMENTS

| | | |
|---|---|---|
| DE | 23 51 815 A1 | 4/1975 |
| DE | 200 04 514 U1 | 8/2001 |
| DE | 10 2004 002 711 A1 | 8/2004 |

(Continued)

OTHER PUBLICATIONS

German Search Report dated Jan. 29, 2008 with English translation (nine (9) pages). International Search Report dated Jun. 16, 2008 with English translation (six (6) pages).

*Primary Examiner* — Lisa Caputo
*Assistant Examiner* — Punam Roy
(74) *Attorney, Agent, or Firm* — Crowell & Moring LLP

(57) ABSTRACT

A protective cap is provided for a sensor having a sensor element, which is disposed in a housing and includes a connection side and a measuring side, for determining gases in gas mixtures. The protective cap delimits a sensor element chamber having at least one flow outlet and an antechamber that has at least one flow inlet and is in fluid connection with the sensor element chamber in order to protect the sensor element on the measuring side. A condensate separator is provided in the antechamber. A device for deviating the flow is provided between the sensor element chamber and the antechamber and a device for accelerating the flow is provided on a flow outlet side of the sensor element chamber. A gas sensor is equipped with the protective cap.

15 Claims, 4 Drawing Sheets

FOREIGN PATENT DOCUMENTS

| | | |
|---|---|---|
| DE | 103 37 840 A1 | 3/2005 |
| DE | 10 2004 033 958 A2 | 2/2006 |
| DE | 10 2004 050 222 A1 | 4/2006 |
| DE | 10 2004 050 630 A1 | 4/2006 |
| DE | 10 2005 012 449 A1 | 9/2006 |
| EP | 0 978 721 A1 | 2/2000 |
| EP | 1 541 999 A1 | 6/2005 |
| JP | 2000-171429 A | 6/2000 |
| JP | 2001-99807 A | 4/2001 |

* cited by examiner

PROTECTIVE CAP FOR A GAS SENSOR, AND A GAS SENSOR

CROSS-REFERENCE TO RELATED APPLICATIONS

This application is a continuation of PCT International Application No. PCT/EP2008/001991, filed Mar. 13, 2008, which claims priority under 35 U.S.C. §119 to German Patent Application No. DE 10 2007 016 976.2, filed Apr. 10, 2007, the entire disclosures of which are herein expressly incorporated by reference.

BACKGROUND AND SUMMARY OF THE INVENTION

The invention relates to a protective cap for a sensor including a sensor element, which is disposed in a housing and includes a connection side and a measuring side, for determining gases in gas mixtures. The protective cap delimits a sensor element chamber and an antechamber in order to protect the sensor element on the measuring side. Furthermore, the invention relates to a gas sensor equipped with a protective cap.

Gas sensors are used for determining gases in gas mixtures by being disposed, for example, in a gas stream so that a part of the gas stream flows past the sensor element. In doing so, protective caps described at the start are used in order to protect sensor elements from undesirable components of the gas mixture and/or to ensure an optimized incident flow at the sensor element.

Gas sensors having a protective cap are the subject matter of DE 10 2004 050 222 A1 and DE 10 2005 012 449 A1 by way of example. However, it has been found that the known protective caps do not protect the sensor element to a sufficient extent and do not ensure a defined incident flow at the sensor element. For example, in a NOx sensor used in a motor vehicle for analyzing the internal combustion-engine exhaust gases, the sensor element can be exposed to condensate particularly during cold start and the warm-up phase, which results in the sensor element being damaged by the deposition of pollutants. A damaged sensor element of this type supplies incorrect or even no signals so that the operation of the internal combustion engine is very adversely affected.

It is therefore the object of the invention to provide a protective cap and a gas sensor in which an entry of undesirable components of the gas mixture is effectively avoided and a defined incident flow at the sensor element is ensured at the same time.

The object is achieved according to the invention with a protective cap for a sensor comprising a sensor element, which is disposed in a housing and has a connection side and a measuring side, for determining gases in gas mixtures. The protective cap delimits a sensor element chamber and an antechamber in order to protect the sensor element on the measuring side. A condensate separator is arranged in the antechamber. Likewise, the object of the invention is achieved with a protective cap for a sensor comprising a sensor element, which is disposed in a housing and has a connection side and a measuring side, for determining gases in gas mixtures. The protective cap delimits a sensor element chamber and an antechamber that is in fluid connection with the sensor element chamber in order to protect the sensor element on the measuring side. A device for deviating the flow is provided between the sensor element chamber and the antechamber. Furthermore, a protective cap achieves the object of the invention by providing a device for accelerating the flow on the flow outlet side of the sensor element chamber.

Particularly preferable embodiments of the invention and a gas sensor having the protective cap of the invention are further described herein.

It is particularly preferred to arrange the at least one flow inlet of the antechamber at the measuring-side end of the antechamber. This measure prevents a dead space in which particles or fluid components could be deposited.

The condensate separator is preferably formed as an annular circumferential rim, which is open axially in the direction of the at least one flow inlet of the antechamber and is disposed on the radially inner wall of the antechamber. By virtue of this arrangement, the gas stream flowing into the antechamber is deviated, particles and/or fluid components of the gas stream being separated from the same. It is very advantageous to arrange the fluid connection between the sensor element chamber and the antechamber axially on the sensor-connection side of the condensate separator. This arrangement necessitates a recirculation area of the flow and thus contributes to the particularly effective separation of particles and/or fluid components of the gas stream.

The device for deviating the flow expediently includes at least one opening with a flow-guiding device. This measure effectively prevents a direct incident flow at the sensor element and thus avoids an uneven cooling of the sensor element.

It has proved to be particularly advantageous to form the device for accelerating the flow as a conical nozzle. The gas stream flowing past the sensor element can be adjusted particularly easily with regard to flow volume and flow velocity by way of a corresponding, constructive design of the conical nozzle.

According to a particularly preferred embodiment of the invention, the ante-chamber includes at least one flow outlet in addition to the at least one flow inlet, it being possible to branch off a partial stream from an incoming gas stream from the antechamber into the sensor element chamber with the aid of the fluid connection between the antechamber and the sensor element chamber. In this way, a defined partial stream can be branched off from the gas stream and routed past the sensor element.

According to a further preferred exemplary embodiment, a baffle plate is disposed upstream of the device for accelerating the flow so that the sensor element is not located directly in front of a flow outlet and, furthermore, the flow experiences a restriction.

According to a further, preferred exemplary embodiment, an additional cap having at least one flow outlet is disposed downstream of the device for accelerating the flow. The additional cap notably prevents the entry of undesirable particles and/or fluid components of the gas stream toward the sensor element through the flow outlet.

A gas sensor including a protective cap of the invention provides special advantages.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
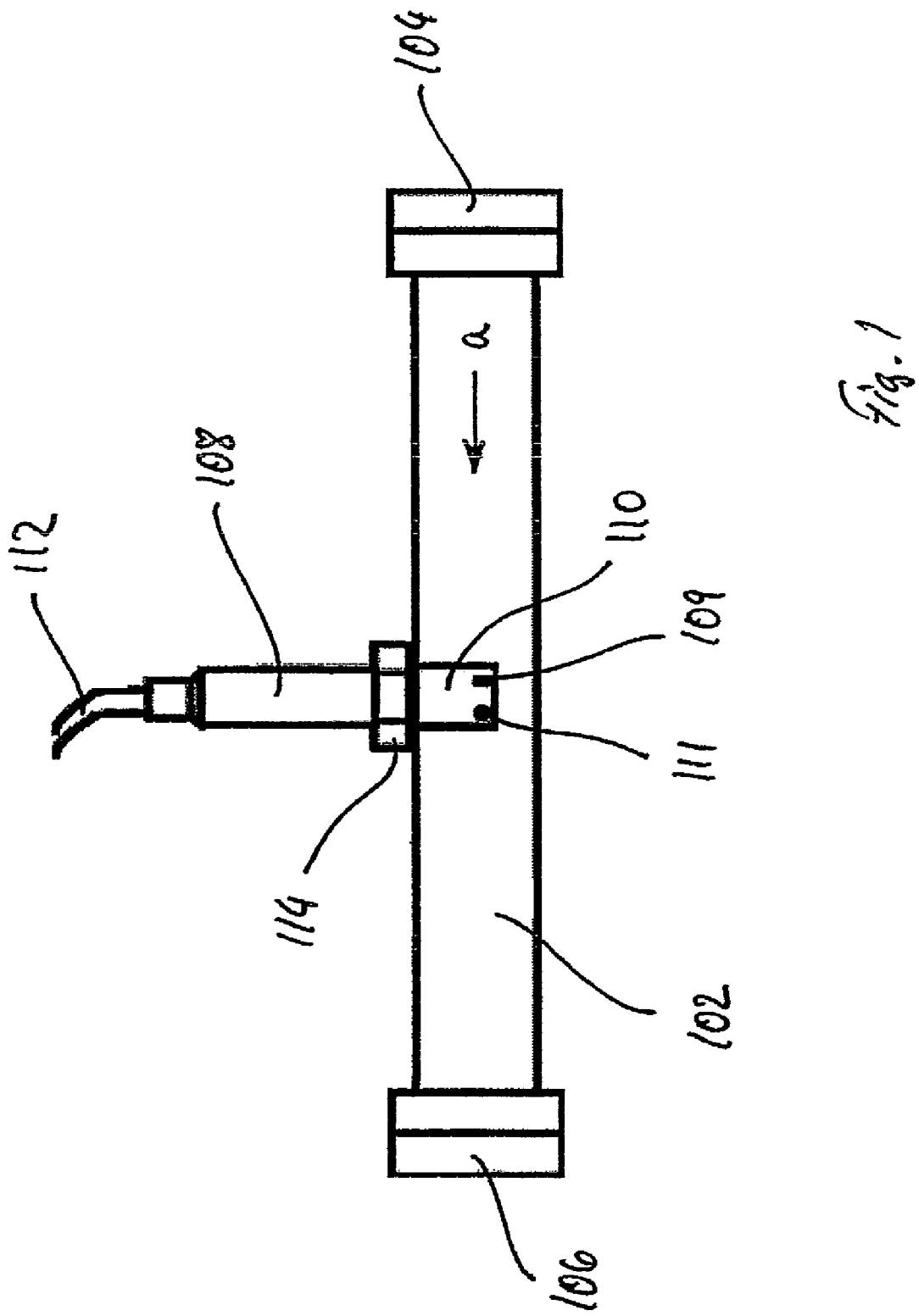
FIG. 1 is a section of an exhaust tract of an internal combustion engine having a gas sensor for determining gases in the exhaust-gas mixture.

FIG. 1 illustrates a section of an exhaust tract (not illustrated in detail) of an internal combustion engine, the exhaust gas stream flowing according to the direction of the arrow "a" through the exhaust pipe 102 starting from a flow inlet 104 toward a flow outlet 106. A gas sensor 108 having a measuring side 110 and a connection side 112 is attached to the exhaust pipe 102 in such a way that its measuring side 110 protrudes into the exhaust gas stream. Inlet ports 109 are provided, through which a part of the exhaust gas stream can flow toward a sensor element. This partial stream can then flow off again through an outlet port 111. For its connection, the gas sensor 108 includes a threaded portion and a connecting flange 114 by way of example, and is screwed into the exhaust pipe 102 from the outside up to the flange stop. A seal is provided between the connecting flange 114 of the gas sensor 108 and the exhaust pipe 102.

In the present case, the sensor 108 is a NOx sensor used for measuring the NOx-concentration in the exhaust gas. A sensor of this type is used in combination with NOx-storage catalytic converters in order to detect the loading and regenerating condition of the catalytic converters. The invention can also be used in combination with other gas sensors such as a lambda sensor used for determining the air-fuel ratio based on the residual oxygen content in the exhaust gas.

Figure 2:
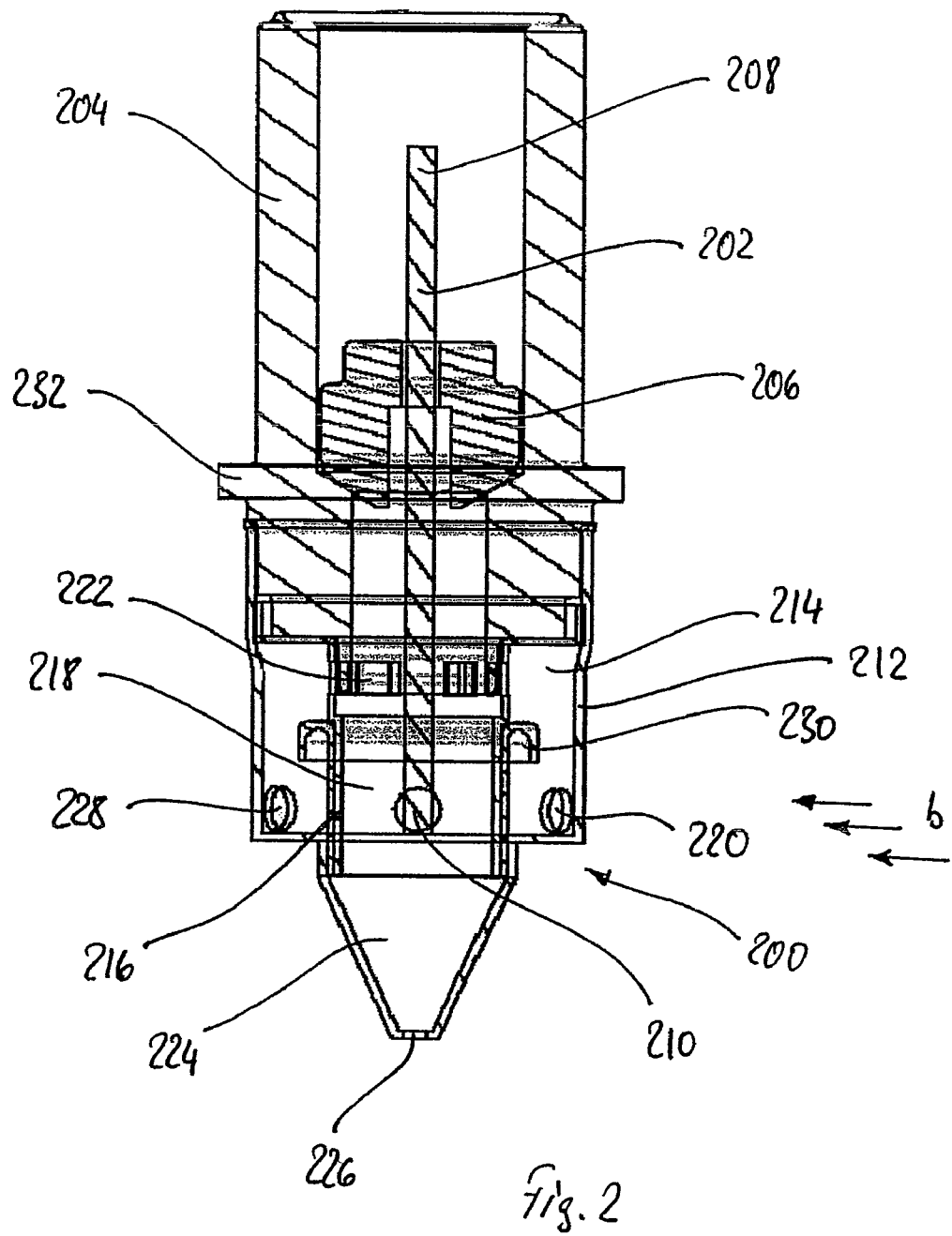
FIG. 2 is a schematic illustration of a gas sensor with a protective cap.
Figure 3:
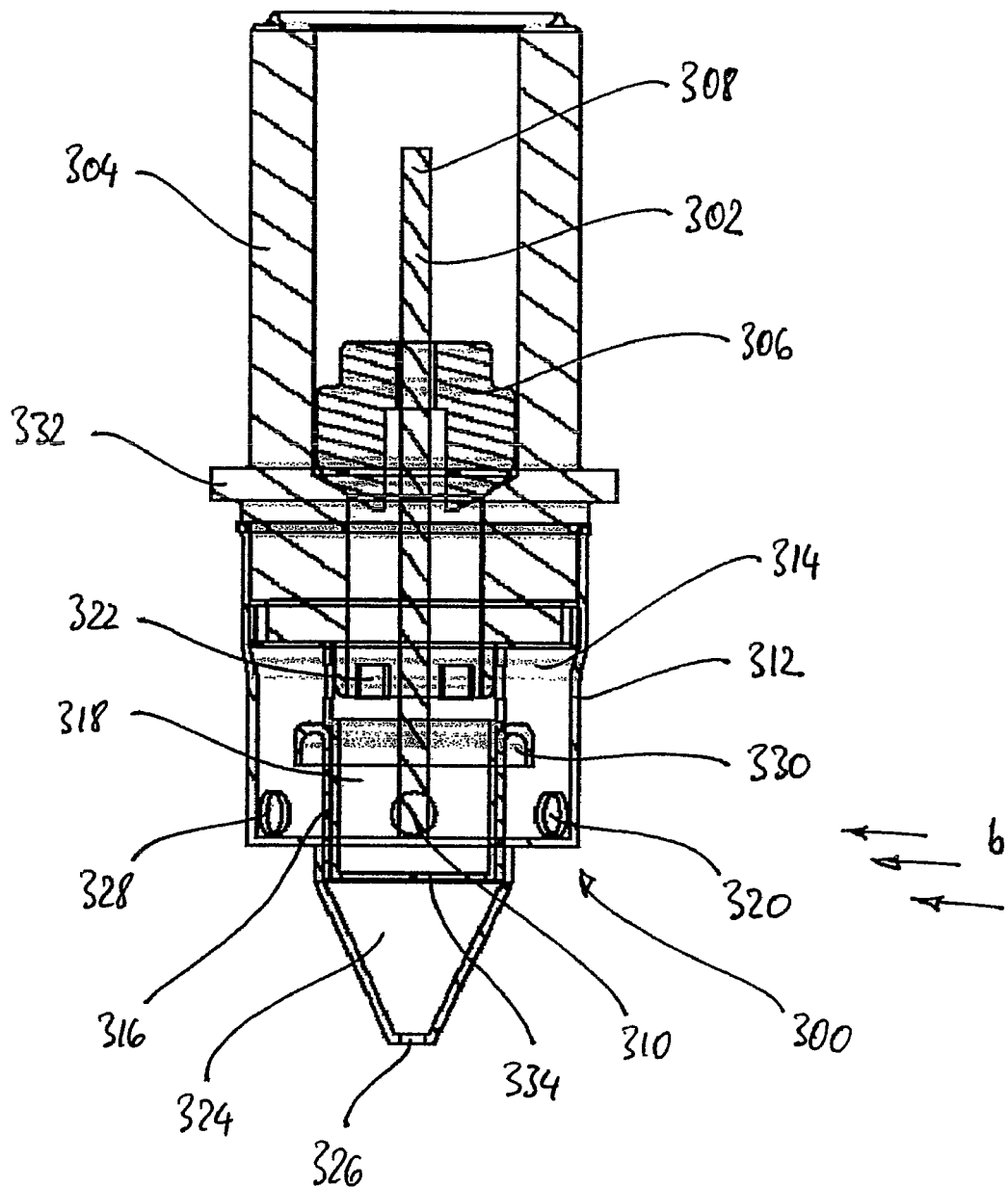
FIG. 3 is a schematic illustration of a gas sensor with a protective cap and a baffle plate.
Figure 4:
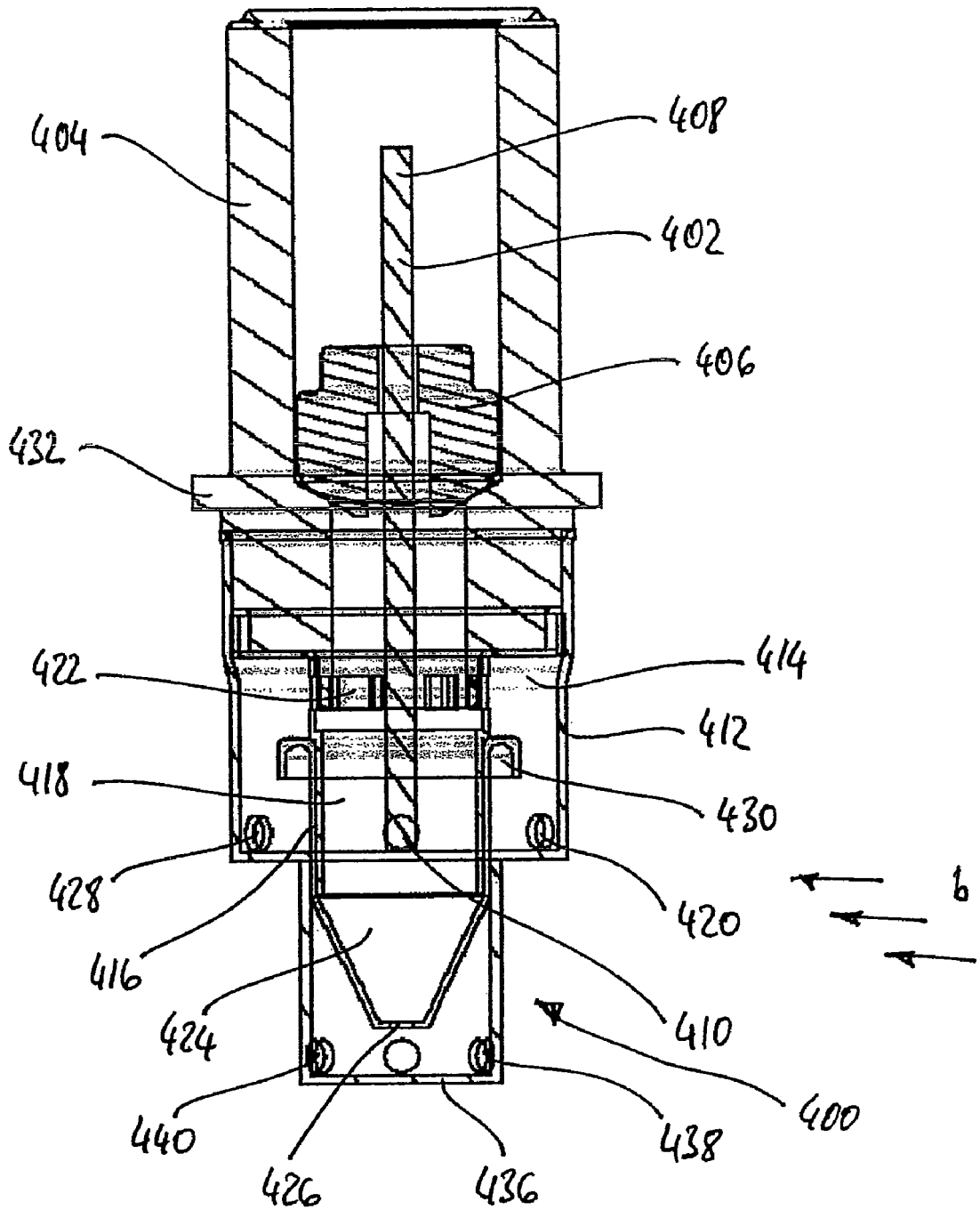
FIG. 4 is a schematic illustration of a gas sensor with a protective cap and an additional cap.

Reference is made to FIGS. 2, 3 and 4 below, each of which shows in detail a gas sensor having a protective cap 200, 300, 400. A sensor element 202, 302, 402 is fixed in the housing 204, 304, 404 of the gas sensor. The sensor element 202, 302, 402 includes a connection-side end 208, 308, 408 and a measuring-side end 210, 310, 410 and is disposed in a gastight manner by way of a seal 206, 306, 406 in the housing 204, 304, 404.

A protective cap 200, 300, 400 protectively surrounds the sensor element 202, 302, 402 and is connected to the housing 204, 304, 404 on the measuring side of the sensor element. The protective cap 200, 300, 400 includes an outer protecting tube 212, 312, 412 and an inner protecting tube 216, 316, 416. The inner protecting tube 216, 316, 416 surrounds the measuring-side end 210, 310, 410 of the sensor element 202, 302, 402. The outer protecting tube 212, 312, 412 in turn surrounds the inner protecting tube 216, 316, 416. The inner protecting tube 216, 316, 416 delimits a sensor element chamber 218, 318, 418; the outer protecting tube 212, 312, 412 together with the inner protecting tube 216, 316, 416 delimits an antechamber 214, 314, 414. The outer protecting tube 212, 312, 412 includes several flow inlets 220, 320, 420 at the measuring-side end of the antechamber 214, 314, 414 in accordance with the incident flow corresponding to the direction of the arrow "b".

A condensate separator 230, 330, 430 is arranged in the antechamber 214, 314, 414. The condensate separator 230, 330, 430 is formed as an annular circumferential rim which is open axially in the direction of the flow inlets 220, 320, 420 of the antechamber 214, 314, 414 and is disposed on the radially inner wall of the antechamber 214, 314, 414, that is to say, or the inner protecting tube 216, 316, 416. Regardless of the name "condensate separator," the latter, in this case, serves for the separation of fluid, in particular, condensate and/or particles from the gas stream to be sensed.

A fluid connection, which, in this case, includes a device 222, 322, 422 for deviating the flow having at least one opening with a flow-guiding device, is provided between the antechamber 214, 314, 414 and the sensor element chamber 218, 318, 418. This fluid connection is produced by bending regions of the inner protecting tube 216, 316, 416 inward in a tongue-like manner forming flow-guiding devices at the same time. According to another exemplary embodiment, the openings can also be formed without any flow-guiding devices or with differently designed flow-guiding devices. However, in doing so, a direct incident flow at the sensor element 202, 302, 402 must be prevented.

A device 224, 324, 424 used for accelerating the flow and formed as a conical nozzle with an outlet 226, 326, 426 is disposed at the measuring-side end of the inner protecting tube 216, 316, 416. The device 224, 324, 424 accelerates the flow in the inner protecting tube 216, 316, 416 so that fluid, in particular, condensate and/or particles that has/have entered the region of the sensor element chamber 218, 318, 418 is/are conveyed by the accelerated flow toward the outlet hole 226, 326, 426. A baffle plate 334 may be disposed upstream of the device for accelerating the flow (see FIG. 3) so that the sensor element 302 is not located directly in front of a flow outlet and, furthermore, the flow experiences a restriction.

During the operation of the internal combustion engine, that is to say, when the exhaust gas flows in the exhaust pipe 102, only a part of the gas stream flowing in through the flow inlets 220, 320, 420 flows from the antechamber 214, 314, 414 further into the sensor element chamber 218, 318, 418. Another partial stream flows directly out of the antechamber 214, 314, 414 through boreholes 228, 328, 428 oriented away from the flow. The volume flowing through the sensor element chamber 218, 318, 418 is determined by way of the device 224, 324, 424 for accelerating the flow and the outlet 226, 326, 426 by generating a defined, predetermined vacuum at the outlet 226, 326, 426 with the aid of a corresponding, constructive design.

The gas stream generating the vacuum at the outlet 226, 326, 426 of the sensor element chamber 218, 318, 418 and the gas stream in the outer protecting tube 212, 312, 412 for withdrawing the sample gas are decoupled. This flow configuration ensures a rapid gas exchange in the antechamber 214, 314, 414 so that fluid, in particular, condensate and/or particles, which has/have penetrated into this outer chamber, is/are again discharged through the boreholes 228, 328, 428 oriented away from the flow.

The flow-guiding devices of the device 222, 322, 422 for deviating the flow prevent a direct incident flow at the sensor element 202, 302, 402 in order to prevent an uneven cooling of the sensor element 202, 302, 402 and thus avoid the risk of destruction due to thermal stresses. A swirl flow is generated with the aid of the flow-guiding devices.

The total area made available to the flow in the sensor element chamber 218, 318, 418 as a result of the openings in the device 222, 322, 422 for deviating the flow is large in comparison to the surface of the outlet hole 226, 326, 426 of the sensor element chamber 218, 318, 418. Thus, there is no momentum provided for generating a swirl flow around the sensor element 202, 302, 402. Alternately, the openings can also be disposed axially in the flow direction. However, in another application of the gas sensor, it may be essential to generate a swirl flow around the sensor element 202, 302, 402.

A recirculation area is generated in the antechamber 214, 314, 414 with the aid of the condensate separator 230, 330, 430. This recirculation area serves for the deposition of fluid drops and solid particles on the outer side of the inner protecting tube 216, 316, 416. Furthermore, the condensate separator 230, 330, 430 prevents the transport of drops deposited on the wall toward the openings of the device 222, 322, 422 for deviating the flow, which transport can take place by way of the flow itself and the vibration of the component due to the excitation of the exhaust system. The effect of the condensate separator 230, 330, 430 is particularly advantageous when the component is still cold. During this critical period of the use of the sensor element 202, 302, 402, a substantial part of the water vapor present in the exhaust gas is deposited in a targeted manner, as a result of the hot ceramic element, at a location that is safe for the sensor.

In the present case, the flow configuration selected permits the minimization of the cavity in the outer protecting tube 212, 312, 412. This minimization, firstly, supports the rapid gas exchange in the outer protecting tube 212, 312, 412 and secondly, leads to a rapid heating of the overall system.

The device 224, 324, 424 formed as conical nozzle for accelerating the flow ensures that fluid, in particular, condensate and/or particles, which has/have penetrated into an additional cap 436 (See FIG. 4) having flow outlets 438, 440, cannot reach the sensor element 202, 302, 402 by way of the outlet hole 226, 326, 426 of the sensor element chamber 218, 318, 418. This is further supported by the effect that independently of the flow direction of the exhaust gas, there is always a gas stream present that is directed outward from the sensor element chamber 218, 318, 418.

The minimization of the size of the additional cap 436 in the region of the core flow of the exhaust gas in combination with good thermal connection leads to a rapid heating of the inner protecting tube 216, 316, 416 and thus a dry sensor element chamber 218, 318, 418.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A component for a sensor having a sensor element disposed in a housing, the sensor element including a connection side and a measuring side for sensing gases in gas mixtures, the component comprising:
    a protective cap delimiting a sensor element chamber in which the sensor element is arranged and an antechamber in order to protect the sensor element on the measuring side; and
    a condensate separator arranged in the antechamber,
    wherein the condensate separator comprises an annular circumferential rim that is open axially in a direction of the at least one flow inlet of the antechamber and closed axially in a direction of the connection side, the annular circumferential rim having an inner side disposed on a radially inner wall of the antechamber and an outer side spaced apart from a radially outer wall of the antechamber.

2. The component according to claim 1, wherein the antechamber comprises at least one flow inlet disposed at the measuring side of the antechamber.

3. The component according to claim 1, wherein a fluid connection between the sensor element chamber and the antechamber is disposed axially on the connection side of the condensate separator.

4. The component according to claim 3, further comprising a flow deviation device operatively arranged between the sensor element chamber and the antechamber in the fluid connection.

5. The component according to claim 4, further comprising a flow acceleration device formed as a conical nozzle, the flow acceleration device being disposed on a flow outlet side of the sensor element chamber.

6. The component according to claim 1, wherein the antechamber comprises at least one flow outlet in addition to at least one flow inlet, wherein a partial stream from an incoming gas stream from the antechamber is branchable off into the sensor element chamber via a fluid connection between the antechamber and the sensor element chamber.

7. A component for a sensor having a sensor element disposed in a housing, the sensor element including a connection side and a measuring side for sensing gases in gas mixtures, the component comprising:
    a protective cap delimiting a sensor element chamber in which the sensor element is arranged and an antechamber in order to protect the sensor element on the measuring side;
    a condensate separator arranged in the antechamber;
    a flow deviation device operatively arranged between the sensor element chamber and the antechamber in the fluid connection;
    wherein the condensate separator comprises an annular circumferential rim that is open axially in a direction of the at least one flow inlet of the antechamber, and is disposed on a radially inner wall of the antechamber,
    wherein the antechamber comprises at least one flow inlet disposed at the measuring side of the antechamber,
    wherein a fluid connection between the sensor element chamber and the antechamber is disposed axially on the connection side of the condensate separator, and further comprising:
    a baffle plate disposed upstream of the flow acceleration device.

8. A component for a sensor having a sensor element disposed in a housing, the sensor element including a connection side and a measuring side for sensing gases in gas mixtures, the component comprising:
    a protective cap delimiting a sensor element chamber in which the sensor element is arranged and an antechamber in order to protect the sensor element on the measuring side;
    a condensate separator arranged in the antechamber,
    a flow deviation device operatively arranged between the sensor element chamber and the antechamber in the fluid connection;
    a flow acceleration device formed as a conical nozzle, the flow acceleration device being disposed on a flow outlet side of the sensor element chamber; and
    wherein the condensate separator comprises an annular circumferential rim that is open axially in a direction of the at least one flow inlet of the antechamber and is disposed on a radially inner wall of the antechamber,
    wherein the antechamber comprises at least one flow inlet disposed at the measuring side of the antechamber,
    wherein a fluid connection between the sensor element chamber and the antechamber is disposed axially on the connection side of the condensate separator, and further comprising:
    an additional cap having at least one flow outlet, the additional cap being disposed downstream of the flow acceleration device.

9. A component for a sensor having a sensor element disposed in a housing, the sensor element including a connection side and a measuring side for sensing gases in gas mixtures, the component comprising:
- a protective cap delimiting a sensor element chamber in which the sensor element is arranged and an antechamber in fluid communication with the sensor element chamber in order to protect the sensor element on the measuring side; and
- a flow deviating device operatively arranged at a connection side of the protective cap between the sensor element chamber and the antechamber, wherein the flow deviating device comprises at least one opening having a flow-guiding device arranged in the fluid connection,
  - a flow acceleration device formed as a conical nozzle, the conical nozzle being disposed on a flow outlet side of the sensor element chamber; and
  - an additional cap having at least one flow outlet, the additional cap being disposed only downstream of the flow acceleration device, wherein the at least one flow outlet of the additional cap is not a flow inlet for the sensor.

10. The component according to claim 9, wherein the antechamber comprises at least flow inlet disposed at the measuring side of the antechamber.

11. The component according to claim 9, wherein the antechamber comprises at least one flow outlet in addition to at least flow inlet, wherein a partial stream from an incoming gas stream from the antechamber is branchable off into the sensor element chamber via a fluid connection between the antechamber and the sensor element chamber.

12. The component according to claim 9, further comprising a baffle plate disposed upstream of the flow acceleration device.

13. A gas sensor, comprising:
- a sensor element disposed in a housing and having a connection side and a measuring side for determining gases in gas mixtures;
- a protective cap delimiting a sensor element chamber and an antechamber in order to protect the sensor element on the measuring side; and
- a condensate separator arranged in the antechamber, wherein the condensate separator comprises an annular circumference rim that is open axially in a direction of the at least one flow inlet of the antechamber and closed axially in a direction of the connection side, the annular circumferential rim having an inner side disposed on a radially inner wall of the antechamber and an outer side spaced apart from a radially outer wall of the antechamber.

14. The gas sensor according to claim 13, further comprising a flow deviation device provided between the sensor element chamber and the antechamber, which chambers are in fluid communication with one another.

15. The gas sensor according to claim 14, further comprising a flow acceleration device disposed on a flow outlet side of the sensor element chamber.

* * * * *